US008988519B2

(12) United States Patent
Mar et al.

(10) Patent No.: US 8,988,519 B2
(45) Date of Patent: Mar. 24, 2015

(54) AUTOMATIC MAGNIFICATION OF DATA ON DISPLAY SCREEN BASED ON EYE CHARACTERISTICS OF USER

(75) Inventors: Murray B. Mar, Issaquah, WA (US); Alan D. Gatzke, Bainbridge Island, WA (US); Ty Thorsen, Seattle, WA (US)

(73) Assignee: Cisco Technology, Inc., San Jose, CA (US)

( * ) Notice: Subject to any disclaimer, the term of this patent is extended or adjusted under 35 U.S.C. 154(b) by 384 days.

(21) Appl. No.: 13/424,866

(22) Filed: Mar. 20, 2012

(65) Prior Publication Data

US 2013/0250086 A1 Sep. 26, 2013

(51) Int. Cl.
| | |
|---|---|
| *H04N 7/18* | (2006.01) |
| *G02B 27/00* | (2006.01) |
| *G06F 3/01* | (2006.01) |
| *A61B 3/113* | (2006.01) |
| *G06K 9/00* | (2006.01) |
| *H04N 5/232* | (2006.01) |
| *A61B 3/14* | (2006.01) |

(52) U.S. Cl.
CPC ............ *G02B 27/0093* (2013.01); *G06F 3/011* (2013.01); *A61B 3/113* (2013.01); *G06K 9/00597* (2013.01); *H04N 5/23219* (2013.01); *G02B 27/00* (2013.01); *G06F 3/013* (2013.01); *G06K 9/00604* (2013.01); *A61B 3/145* (2013.01)
USPC .................... 348/78; 348/76; 348/77; 348/79

(58) Field of Classification Search
CPC .......... A61B 3/10; A61B 3/113; A61B 3/145; G02B 27/0093; G06F 3/011; G06F 3/013; G06K 9/00604; G06K 9/00597; H04N 5/23219

USPC .......................................... 348/78, 79–82, 77
See application file for complete search history.

(56) References Cited

U.S. PATENT DOCUMENTS

| | | | | |
|---|---|---|---|---|
| 4,075,657 | A * | 2/1978 | Weinblatt | 348/78 |
| 5,325,133 | A * | 6/1994 | Adachi | 351/209 |
| 5,365,302 | A * | 11/1994 | Kodama | 396/51 |
| 5,623,703 | A * | 4/1997 | Takagi et al. | 396/51 |
| 5,905,525 | A * | 5/1999 | Ishibashi et al. | 348/39 |
| 6,091,546 | A * | 7/2000 | Spitzer | 359/618 |
| 6,456,262 | B1 * | 9/2002 | Bell | 345/8 |
| 6,603,491 | B2 * | 8/2003 | Lemelson et al. | 715/784 |
| 7,688,954 | B2 | 3/2010 | Gatzke et al. | |
| 7,855,743 | B2 * | 12/2010 | Sako et al. | 348/333.02 |
| 7,931,373 | B2 * | 4/2011 | Hillis et al. | 351/246 |
| 8,408,706 | B2 * | 4/2013 | Yahav | 351/210 |
| 8,562,540 | B2 * | 10/2013 | Goodall et al. | 600/558 |

(Continued)

OTHER PUBLICATIONS

Eye-tracking, http://en.wikipedia.org/wiki/Eye_tracking, 2014.*

(Continued)

*Primary Examiner* — Andy Rao
*Assistant Examiner* — Shan Elahi
(74) *Attorney, Agent, or Firm* — Cindy Kaplan

(57) ABSTRACT

In one embodiment, a method includes receiving an image of a user's eye at a device having a screen and a camera operable to input the image, processing the image to identify one or more characteristics of the user's eye for use in determining if the user is having difficulty viewing data displayed on the screen, and magnifying the data displayed on the screen if the user is having difficulty viewing the data. An apparatus and logic are also disclosed.

20 Claims, 4 Drawing Sheets

(56) References Cited

U.S. PATENT DOCUMENTS

| | | |
|---|---|---|
| 8,847,988 B2* | 9/2014 | Geisner et al. ............... 345/633 |
| 2002/0109782 A1* | 8/2002 | Ejima et al. ............. 348/333.01 |
| 2003/0149549 A1* | 8/2003 | Paxton et al. ................ 702/186 |
| 2004/0130645 A1* | 7/2004 | Ohmura et al. .......... 348/333.08 |
| 2004/0189938 A1* | 9/2004 | Eagan .......................... 351/208 |
| 2004/0196399 A1* | 10/2004 | Stavely .................... 348/333.01 |
| 2004/0227822 A1* | 11/2004 | Cartlidge et al. ........ 348/207.99 |
| 2005/0199783 A1* | 9/2005 | Wenstrand et al. ........ 250/214.1 |
| 2009/0018419 A1* | 1/2009 | Torch ............................ 600/318 |
| 2009/0271732 A1* | 10/2009 | Kondo et al. ................ 715/781 |
| 2010/0091139 A1* | 4/2010 | Sako et al. .............. 348/231.99 |
| 2010/0097573 A1* | 4/2010 | Verdooner et al. ........... 351/206 |
| 2010/0110311 A1* | 5/2010 | Sade et al. .................... 348/750 |
| 2010/0114076 A1* | 5/2010 | Reinstein et al. ................. 606/4 |
| 2010/0149073 A1* | 6/2010 | Chaum et al. ..................... 345/8 |
| 2010/0171808 A1 | 7/2010 | Harrell et al. |
| 2010/0208942 A1* | 8/2010 | Porter et al. .................. 382/106 |
| 2010/0290668 A1* | 11/2010 | Friedman et al. ............. 382/103 |
| 2011/0149097 A1* | 6/2011 | Danuser et al. ............ 348/222.1 |
| 2012/0008169 A1* | 1/2012 | Fredlund et al. ............. 358/1.15 |

OTHER PUBLICATIONS

C. Harrison et al., "Lean and Zoom: Proximity-Aware User Interface and Content Magnification", Carnegie Melon University, CHI 2008, Apr. 5-10, 2008, Florence, Italy.

\* cited by examiner

AUTOMATIC MAGNIFICATION OF DATA ON DISPLAY SCREEN BASED ON EYE CHARACTERISTICS OF USER

TECHNICAL FIELD

The present disclosure relates generally to display of data on an electronic device, and more particularly, to magnification of the data for ease of use of the electronic device.

BACKGROUND

Electronic devices such as handheld or mobile devices are increasingly used for many applications. Due to their compact size, many of these devices have small display screens. As people get older, they often need reading glasses to view data on the small screen. However, glasses are often misplaced or forgotten. If glasses are not available, the user may squint their eyes in an attempt to focus on the data displayed on the screen. Zoom features are available on many electronic devices, however, they may not be easily accessed or activated. Thus, it may be easier for a user to simply squint in an attempt to focus on the data. While this may be a quick fix, this does not work well for extended viewing on the electronic device.

BRIEF DESCRIPTION OF THE DRAWINGS

Corresponding reference characters indicate corresponding parts throughout the several views of the drawings.

Description Of Example Embodiments

Overview

Figure 1A:
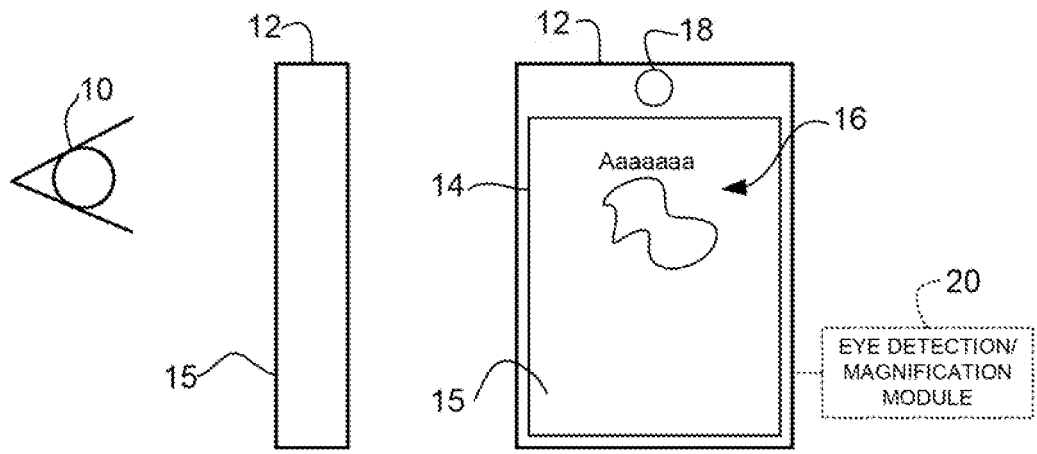
FIGS. 1A and 1B illustrate an example of changes in the appearance of data displayed on a screen based on detection of eye characteristics of a user.

In one embodiment, a method generally comprises receiving an image of a user's eye at a device comprising a screen and a camera operable to input the image, processing the image to identify one or more characteristics of the user's eye for use in determining if the user is having difficulty viewing data displayed on the screen, and magnifying the data displayed on the screen if the user is having difficulty viewing the data.

In another embodiment, an apparatus generally comprises a screen for displaying data, a camera for capturing an image of a user's eye, and a processor for processing the image to identify one or more characteristics of the user's eye for use in determining if the user is having difficulty viewing data displayed on the screen and magnifying the data displayed on the screen if it the user is having difficulty viewing the data.

Example Embodiments

The following description is presented to enable one of ordinary skill in the art to make and use the embodiments. Descriptions of specific embodiments and applications are provided only as examples, and various modifications will be readily apparent to those skilled in the art. The general principles described herein may be applied to other applications without departing from the scope of the embodiments. Thus, the embodiments are not to be limited to those shown, but are to be accorded the widest scope consistent with the principles and features described herein. For purpose of clarity, details relating to technical material that is known in the technical fields related to the embodiments have not been described in detail.

Electronic devices used to display data (e.g., text, graphics, images) often have small screens so that the devices can be portable or take up minimal space. Users often squint in an attempt to bring data on the display screen into focus. Squinting reduces the amount of peripheral light coming into the eye so that a greater percentage of light comes from the center of the visual field. Light rays entering the eye are brought into focus on the retina by refraction by the cornea and the lens which is located behind the iris. When a person needs glasses, many of the light rays are not being focused on the retina. However, the light rays that pass directly through the center visual axis of the cornea and lens are in focus on the retina. When a person squints, their eyelids partially cover the pupils, reducing their size. Squinting, therefore, blocks out the peripheral rays that are not in focus and allows the central rays to be in focus on the retina. When a user of the electronic device squints, it is an indication that the user is having difficulty viewing data displayed on the screen.

The embodiments described herein provide for automatic magnification of data displayed on an electronic device based on eye characteristics of the user. As described below, the device includes a display screen and a forward facing camera that is used to capture an image of one or both of the user's eyes for use in determining if the user is having difficulty viewing the screen. The eye characteristic may include, for example, eye squint or the presence or absence of glasses or contact lenses. In one embodiment, in response to detecting eye squint by the user, the device automatically magnifies data displayed on the screen. The embodiments may eliminate the need for reading glasses when using the electronic device. This is useful, for example, for elderly persons that need magnification but may also have difficulty with a manual zoom operation on the device.

Figure 1B:
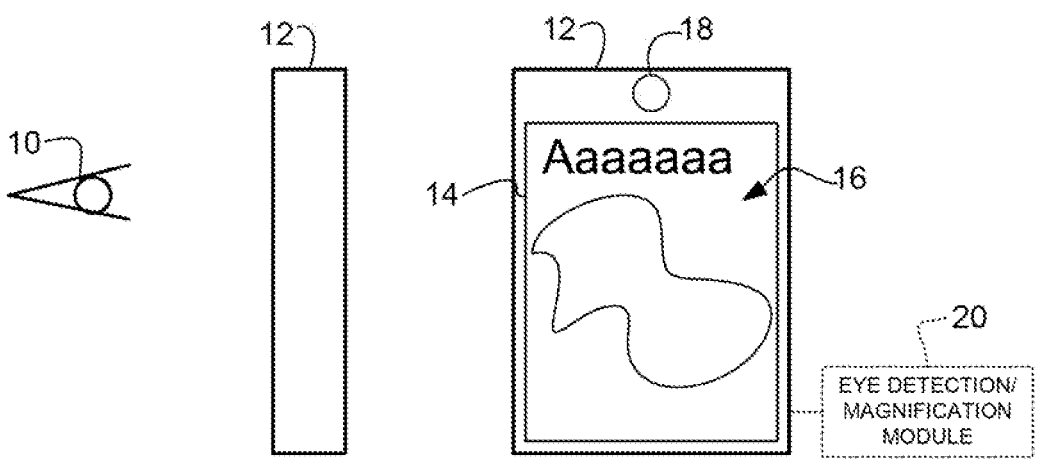

Referring now to the drawings, and first to FIGS. 1A and 1B, an example of changes to data on a display screen based on the user's eye characteristics is shown. The user is viewing an electronic device 12 having a display screen 14 for viewing data generally indicated at 16. The device 12 also includes a forward facing camera 18 (i.e., facing same general direction as the screen 14 or located on same surface 15 as the screen). In the example shown in FIG. 1A, the electronic device 12 is a handheld device comprising a screen 14 that covers the majority of a front face 15 of the device. It is to be understood that this is only an example, and the electronic device 12 may be other types of devices comprising a display screen 14 and forward facing camera 18. The electronic device 12 may be, for example, a handheld device, portable computing device, mobile device, or a desktop device. For example, the electronic device 12 may be any suitable equipment, including, a cellular phone, personal digital assistant, tablet, electronic reading device (e-reader), mobile collaboration device, multimedia device, laptop computer, desktop computer, and the like. Details of one example of the electronic device 12 are described below with respect to FIG. 3.

Referring again to FIG. 1A, a schematic view of an eye 10 in a normal open position (e.g., no eye squint) is shown. The data 16 displayed on the screen 14 in FIG. 1A is generally small and may be, for example, a default font or image size typically used for data displayed on the screen. FIG. 1B illustrates the eye 10 when the user is squinting in an attempt to view the data 16. The user may have difficulty in bringing the image 16 into focus and therefore squints his eyes. As described in detail below, the device 12 includes an eye detection and magnification module 20 operable to identify eye squint (or other eye characteristic) and magnify the data 16 displayed on the screen 14, as shown in FIG. 1B.

Figure 2A:
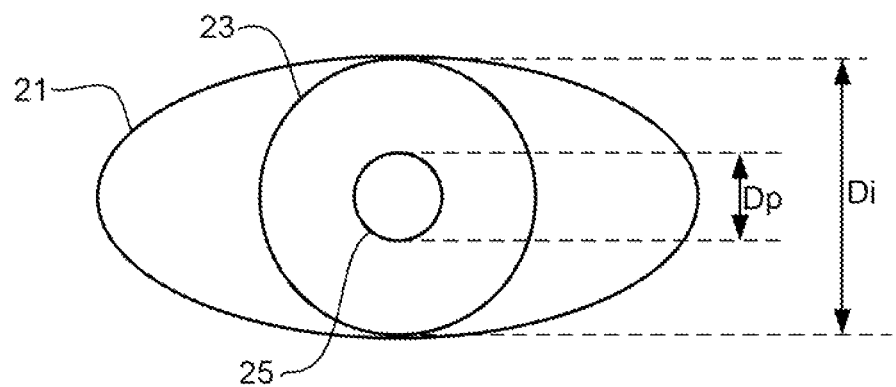
FIGS. 2A and 2B illustrate an example of eye image parameters for use in detecting changes in eye characteristics.
Figure 2B:
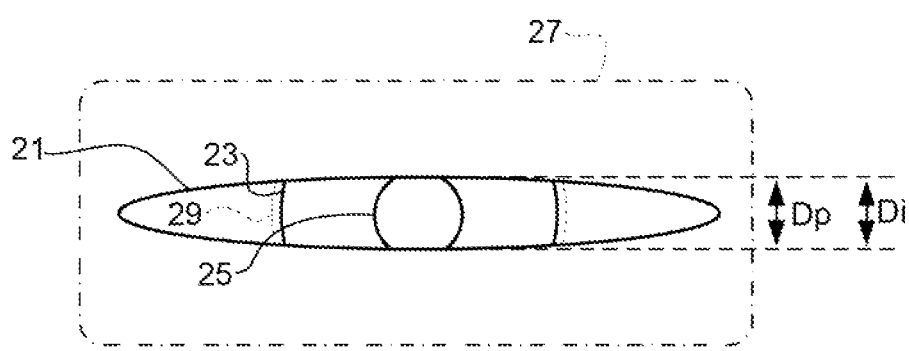

FIGS. 2A and 2B illustrate an example of eye characteristics identified on an eye image 21 for use in determining if the user is having difficulty viewing data 16 displayed on the screen 14 (as shown in FIGS. 1A and 1B). In one embodiment, the eye detection and magnification module 20 is configured to detect one or both of the user's eyes 10 and identify a normal image (FIG. 2A) and a squint image (FIG. 2B). The image may be used to measure one or more parameters which can be stored and compared to a current image of the user's eye to identify if the user is squinting. The parameters may include, for example, the diameter Di of the iris 23 exposed by the eyelids in the normal position (FIG. 2A) and in the squint position (FIG. 2B) or the diameter Dp of the pupil 25 exposed in the normal position and the squint position. The parameter Di also represents the distance between the upper and lower eyelids or exposed portion of the user's eye (iris/pupil). In the example shown in FIG. 2B, the eyelids cover a portion of the iris, thus, Dp is equal to Di.

If a baseline image (FIG. 2A) or parameters are not available for comparison to a current eye image, eye squint may be identified based on the difference between Di and Dp. For example, if Di-Dp is close or equal to zero, eye squint may be detected. If a baseline image is available, changes in Di or Dp may be used to detect eye squint.

The eye detection and magnification module 20 may also be configured to identify positions between the normal state (FIG. 2A) and squint state (FIG. 2B) to provide varying levels of magnification based on the amount of eye squint at the user eye. For example, the percent of magnification may be proportional to the extent of eye squint, with the magnification increasing as the amount of eye squint increases (i.e., Di and Dp decrease).

The eye detection and magnification module 20 is preferably configured to identify parameters for images captured from a range of viewing angles. For example, three-dimensional sensors may be used to capture information about the shape of the eye. Any of the eye's visible features may be used to identify parameters, such as the boundary between the sclera (white portion of eye) and iris or the outline of the pupil against the iris.

The eye detection and magnification module 20 may also be configured to detect other eye characteristics such as whether or not the user is wearing glasses 27 or contact lenses 29 (shown in phantom in FIG. 2B).

It is to be understood that the characteristics and parameters shown in FIGS. 2A and 2B and described above are only examples and any combination of these or other parameters may be used to determine if the user is having difficulty viewing the data. Also, different users of the device 12 may be identified in case multiple users operate the same device, as described further below.

Figure 3:
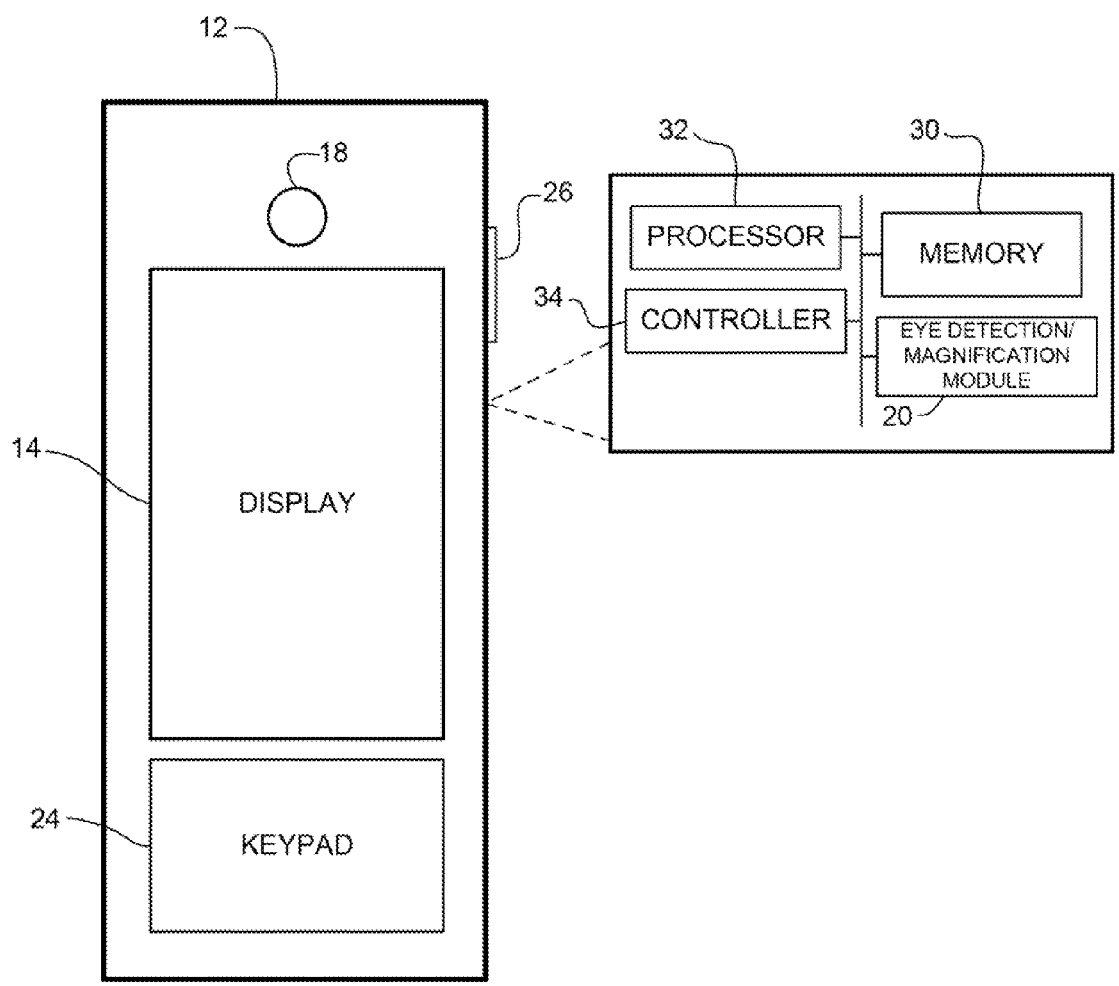
FIG. 3 depicts an example of an electronic device useful in implementing embodiments described herein.

FIG. 3 illustrates an example of the electronic device 12 in which embodiments described herein may be implemented. The device 12 includes the visual display 14 and a keypad 24 comprising multiple keys (not shown) used in operation of the device. The keypad 24 may also be a touch screen integrated with the display 14. The keypad 24 may include numeric keys, alphabetic keys, standard telephone keys, or any other icons or symbols. The device 12 may include any number of other user interfaces such as one or more manual buttons (e.g., switch 26).

The display screen 14 may be integral with the device 12 as shown in FIG. 3, or may be physically separate and coupled to a processing portion of the device (as with a desktop computer, for example).

In one embodiment, the eye detection and magnification module 20 may be configured for displaying a graphical user interface on the display screen 14 for use in calibrating the module (described below). For example, the graphical user interface may present the user with a list of options for use in calibrating the module 20 or activating the module 20, or once active, the user may have the option to stop the magnification process.

One or more external ports (not shown) may be provided for connection with another input or output device. The device 12 may also include a speaker and microphone (not shown).

As illustrated in the block diagram of FIG. 3, the device 12 further includes memory 30, one or more processors 32, device controller 34, and eye detection and magnification module 20. The eye detection and magnification module 20 may be software, application, code, program, device, or any combination thereof.

Memory 30, which may include one or more computer readable storage mediums, may be any form of volatile or nonvolatile memory, including for example, electronic (e.g., RAM (random access memory), ROM (read-only memory), EPROM (erasable programmable read-only memory)), magnetic, optical, flash, electromagnetic, semiconductor technology, or any other suitable medium. Memory 30 may store any data or information, including software and encoded logic, utilized by the electronic device 12. Memory 30 may also store user eye image data gathered during a calibration process described below.

The one or more processors 32 run or execute various codes, software programs, or instructions stored in memory 30 to perform functions for the device 12 and to process data. Logic may be encoded in one or more tangible media for execution by the processor 32. For example, the processor 32 may execute codes stored in a computer-readable medium such as memory 30. Memory 30 can be utilized to store and retrieve software programs incorporating computer code that implements aspects of the embodiments, data for use with the embodiments, and the like.

The processor 32 also includes an image processing component for processing the images received from the camera 18. As described below, the processor 32 is configured to process an image of the user's eye received from the camera 18 for use in determining if the user is having difficulty viewing data on the display screen 14.

The camera 18 may be a charge-coupled device (CCD) that provides an image of the eye 10, which is processed by the image processor to identify eye characteristics. The camera 18 is electrically coupled to the processor 32 for digitization and processing of the digitized image data. For example, the image processing may be used to interpret Di or Dp as captured by the camera 18. The camera 18 may be integral with the device 12, as shown in FIG. 3, or may be mounted on or near the device and electronically coupled to the device.

The device controller 34 provides for management and control of various elements within the device 12. For example, the controller 34 may access information maintained within memory 30 and control other elements to interact with users and other communication devices. The controller 34 may, for example, receive input from the eye detection and magnification module 20 and control a zoom command for the display screen 14 in response to the input from the module.

The device 12 may further include an antenna for wireless communication, RF (Radio Frequency) circuitry, and one or more network interfaces (not shown). The RF circuitry receives and transmits RF signals and converts electrical signals to or from electromagnetic signals and communicates with communication devices via the electromagnetic signals. Communication circuitry allows the device 12 to communicate with other network devices using any suitable communications protocol. The network interface may comprise, for example, a wired interface, a radio interface (e.g., 3G/4G radio interface) for communication via a base station, or a Wi-Fi interface for communication with an access point. The interface may be used, for example, to access user information (e.g., baseline eye parameters) stored in a central database for use with multiple devices operated by the user.

It is to be understood that the device 12 shown in FIG. 3 and described herein is only one example, and that the device may have additional, fewer, or different components, or a different arrangement or configuration of components, without departing from the scope of the embodiments. For example, the device 12 may further include any suitable combination of hardware, software, algorithms, processors, devices, components, or elements operable to facilitate the capabilities described herein. Also, the device may be a desktop device (e.g., personal computer), handheld device without network connectivity, or any other device comprising a display screen 14, forward facing camera 18, and processing capabilities to perform the operations described herein (i.e., eye detection, data magnification).

Figure 4:
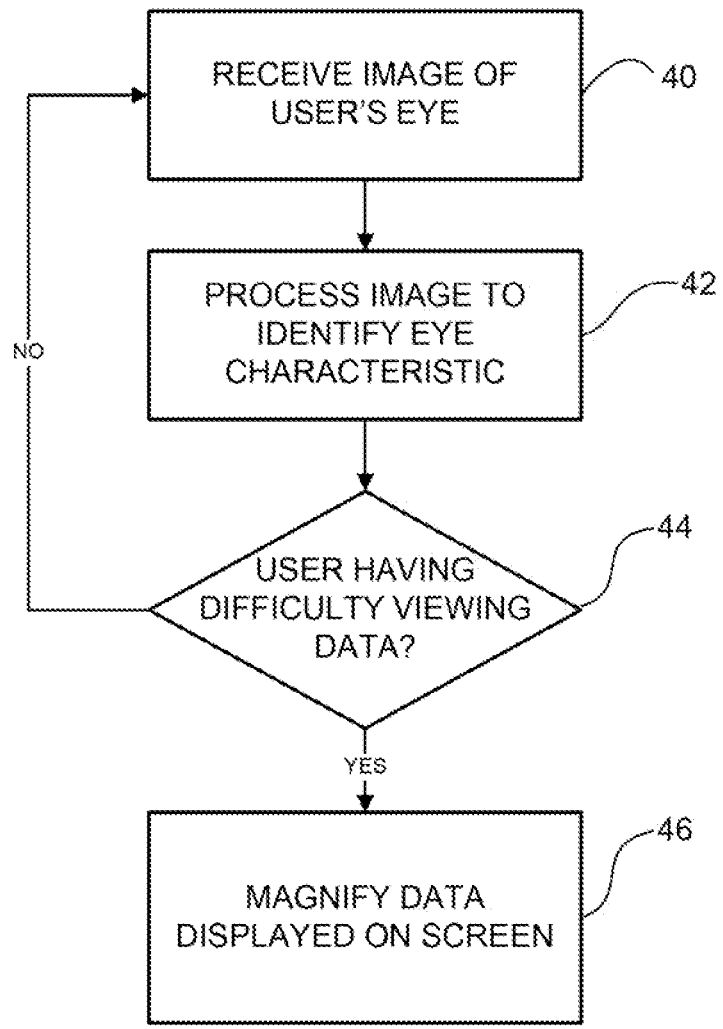
FIG. 4 is a flowchart illustrating an overview of a process for automatic magnification of data based on eye characteristics of the user, in accordance with one embodiment.

FIG. 4 is a flowchart illustrating an overview of a process for automatic magnification of data based on eye characteristics of a user, in accordance with one embodiment. At step 40, the electronic device 12 receives an image of a user's eye from the camera 18. The device 12 processes the image to identify one or more characteristics of the user's eye for use in determining if the user is having difficulty viewing data displayed on the screen 14 (steps 42 and 44). If it is determined that the user is having difficulty viewing the data based on the identified characteristics, the data is magnified on the display screen (step 46). The magnification may be a predefined zoom level or a percentage of magnification based on comparison of the current eye characteristics with previously defined baseline characteristics. If the user is not having difficulty viewing the data based on the identified characteristics, no magnification is needed and the device continues to monitor the user's eye.

It is to be understood that the process illustrated in FIG. 4 is only an example and that steps may be modified, added, or combined, without departing from the scope of the embodiments.

In one embodiment, the eye image is continuously monitored using a video camera. Images are preferably captured and analyzed at periodic intervals so that eye blinks or other temporary changes in eye position are not misinterpreted as eye squint. Also, once eye squint is detected and the data is magnified, magnification preferably continues for all data displayed on the screen until the user interrupts the magnification (e.g., stops magnification process by selecting option on screen or other user interface). Since the user no longer has to squint when the image is displayed, the lack of eye squint should not be used to signal the eye detection and magnification module 20 to stop magnification of the data.

In one embodiment, the eye detection and magnification module 20 includes image detection software operable to locate a user's eye (or eyes) within the input video captured by the camera 18. Many image detection methods are known by those skilled in the art and may be used.

The eye detection and magnification module 20 may be configured to perform a calibration process with the user to provide a baseline image for use in comparison with a current eye image. In one example, upon initiation of the eye detection and magnification application, a calibration image (e.g., eye chart) is presented to the user. For example, text with a large font size may be presented to the user while the camera 18 captures the image of the user's eye viewing the text. The text font size is then reduced, until the user's eyes start to squint. The eye detection and magnification module 20 can then store a normal eye image (or parameters) and the squint eye image for use in identifying a state (e.g., normal, squint) of the user's eye. The calibration process may also be used to identify a percentage of magnification needed based on a percentage of eye squint. Once the calibration process is complete, the camera 18 continuously monitors the user's eye, and the eye detection and magnification module 20 uses the information collected during the calibration process to adjust the display magnification accordingly.

The user may perform additional calibration processes to identify a different set of parameters for use when the user is wearing glasses or contact lenses. The eye detection and magnification module 20 would then identify based on the processed image, whether or not the user is wearing glasses or contact lenses and use a different set of parameters based on this information. The presence or absence of glasses may also be used as an indication that the user is having difficulty viewing the data. For example, if the user removes his glasses (e.g., removes glasses used to see at a distance to help in viewing data on the display screen), this may be interpreted as an eye characteristic indicating that the user is having difficulty viewing the display, in which case the data is magnified.

The calibration process may also be used to identify multiple users of the device and apply parameters according to the specific user operating the device. For example, facial recognition algorithms may identify faces by extracting landmarks for features from an image of the user's face. The algorithm may analyze the relative position, size, or shape of the eyes, nose, cheekbones, and jaw, for example. These features are then used to search for other images with matching features. In this way, the user can be identified and the parameters recorded during calibration, can be used to determine if the current user is having difficulty viewing the data.

The embodiments may also be used in combination with other detection features such as proximity detection. For example, if the user moves the device 12 away from their eyes, the data may revert back to its original unmagnified view.

Although the method and apparatus have been described in accordance with the embodiments shown, one of ordinary skill in the art will readily recognize that there could be variations made without departing from the scope of the embodiments. Accordingly, it is intended that all matter contained in the above description and shown in the accompanying drawings shall be interpreted as illustrative and not in a limiting sense.

What is claimed is:

1. A method comprising:
    receiving an image of a user's eye at a user device comprising a display screen and a camera operable to input said image;
    processing said image to identify one or more characteristics of the user's eye for use in determining if the user is having difficulty viewing data displayed on the display screen of the user device; and magnifying the data displayed on the display screen if the user is having difficulty viewing the data, wherein magnifying the data comprises applying a predefined zoom level to the data.

2. The method of claim 1 wherein determining if the user is having difficulty viewing the data comprises identifying eye squint.

3. The method of claim 1 wherein said one or more characteristics comprises a measurement of an exposed portion of the user's eye.

4. The method of claim 1 wherein said one or more characteristics comprises a measurement of a pupil of the user's eye.

5. The method of claim 1 further comprising detecting if the user is wearing glasses or contact lenses.

6. The method of claim 1 further comprising calibrating said magnification based on different images of the user's eye in combination with data displayed on the screen with different magnifications.

7. An apparatus comprising:
a display screen for displaying data at a user device;
a camera for capturing an image of a user's eye; and
a processor for processing said image to identify one or more characteristics of the user's eye for use in determining if the user is having difficulty viewing the data displayed on the display screen and magnifying the data if the user is having difficulty viewing the data, wherein magnifying the data comprises applying a predefined zoom level to the data.

8. The apparatus of claim 7 wherein determining if the user is having difficulty viewing the data comprises identifying eye squint.

9. The apparatus of claim 7 wherein said one or more characteristics comprises a measurement of an exposed portion of the user's eye.

10. The apparatus of claim 7 wherein said one or more characteristics comprises a measurement of a pupil of the user's eye.

11. The apparatus of claim 7 wherein the processor is further configured to detect if the user is wearing glasses or contact lenses.

12. The apparatus of claim 7 wherein the processor is further configured to calibrate said magnification based on different images of the user's eye in combination with data displayed on the screen with different magnifications.

13. The apparatus of claim 7 further comprising memory for storing baseline parameters for use in comparison with parameters identified in said received image.

14. Logic encoded on one or more non-transitory computer readable media for execution and when executed operable to:
receive at a user device an image of a user's eye from a camera;
process said image to identify one or more characteristics of the user's eye for use in determining if the user is having difficulty viewing data displayed on a display screen at the user device; and
magnify the data displayed on the screen if the user is having difficulty viewing the data, wherein magnifying the data comprises applying a predefined zoom level to the data.

15. The logic of claim 14 wherein determining if the user is having difficulty viewing the data comprises identifying eye squint.

16. The logic of claim 14 wherein said one or more characteristics comprises a measurement of an exposed portion of the user's eye.

17. The logic of claim 14 wherein said one or more characteristics comprises a measurement of a pupil of the user's eye.

18. The logic of claim 14 wherein the logic is operable to identify if the user is wearing glasses or contact lenses.

19. The logic of claim 14 wherein the logic is operable to calibrate said magnification based on different images of the user's eye in combination with data displayed on the screen with different magnifications.

20. The logic of claim 14 wherein the logic is operable to identify the user.

* * * * *